United States Patent
Chamberlain

(10) Patent No.: US 10,226,177 B2
(45) Date of Patent: Mar. 12, 2019

(54) MOBILITY AID MONITORING SYSTEM WITH MOTION SENSOR AND TRANSCEIVER

(71) Applicant: Auto-Pilot Medical Technologies, Inc., Grand Forks, ND (US)

(72) Inventor: Peter Thomas Chamberlain, Grand Forks, ND (US)

(73) Assignee: Auto-Pilot Medical Technologies, Inc., Grand Forks, ND (US)

(*) Notice: Subject to any disclaimer, the term of this patent is extended or adjusted under 35 U.S.C. 154(b) by 0 days.

(21) Appl. No.: 15/853,342

(22) Filed: Dec. 22, 2017

(65) Prior Publication Data
US 2018/0333052 A1    Nov. 22, 2018

Related U.S. Application Data

(60) Provisional application No. 62/509,167, filed on May 21, 2017.

(51) Int. Cl.
*G08B 21/00* (2006.01)
*A61B 5/00* (2006.01)
(Continued)

(52) U.S. Cl.
CPC .......... *A61B 5/0026* (2013.01); *A61B 5/0015* (2013.01); *A61B 5/112* (2013.01);
(Continued)

(58) Field of Classification Search
CPC ..... A61B 5/0026; A61B 5/0015; A61B 5/112; A61B 5/6887; G08B 21/0461
(Continued)

(56) References Cited

U.S. PATENT DOCUMENTS 7,963,294 B1 * 6/2011 Trout ........................ A61H 3/00
135/66
8,702,567 B2    4/2014 Hu et al.
(Continued)

FOREIGN PATENT DOCUMENTS

CN    203468972 U    3/2014
CN    104240441 A    12/2014
(Continued)

*Primary Examiner* — Mark S Rushing
(74) *Attorney, Agent, or Firm* — Brake Hughes Bellermann LLP

(57) ABSTRACT

Systems, apparatuses, devices, and methods for monitoring mobility aids are provided. An example apparatus includes a wheel attachment assembly, a motion sensor, and a transceiver. The wheel attachment assembly is configured to removably attach to a wheel of a mobility aid. The motion sensor is configured to measure rotation of the wheel attachment assembly. The transceiver is in electronic communication with the motion sensor and configured to transmit data based on measurements from the motion sensor. An example system includes a monitoring device and a stationary communication node. The monitoring device is configured to removably attach to a mobility aid and includes a transceiver and a motion sensor configured to measure motion of the monitoring device. The stationary communication node is configured to communicate with the monitoring device. An example method generates alerts based on data from an attachable monitoring device.

22 Claims, 15 Drawing Sheets

(51) Int. Cl.
  *G08B 21/04* (2006.01)
  *A61B 5/11* (2006.01)
(52) U.S. Cl.
  CPC ........ *A61B 5/6887* (2013.01); *G08B 21/0461*
    (2013.01); *A61G 2203/36* (2013.01)
(58) Field of Classification Search
  USPC ....................................................... 340/501
  See application file for complete search history.

(56) References Cited

U.S. PATENT DOCUMENTS

| | | | |
|---|---|---|---|
| 9,180,063 B2 | 11/2015 | Friedman | |
| 9,386,830 B2 | 7/2016 | Crowhurst | |
| 9,773,330 B1* | 9/2017 | Douglas | G06T 11/206 |
| 2002/0013517 A1* | 1/2002 | West | G16H 40/20 |
| | | | 600/300 |
| 2004/0095251 A1* | 5/2004 | Jackson | G08B 21/0446 |
| | | | 340/686.6 |
| 2005/0077345 A1* | 4/2005 | March | G01C 22/02 |
| | | | 235/95 R |
| 2009/0322513 A1* | 12/2009 | Hwang | A61B 5/02055 |
| | | | 340/539.12 |
| 2011/0023920 A1 | 2/2011 | Bolton | |
| 2012/0143400 A1* | 6/2012 | Hinkel, III | B62D 1/00 |
| | | | 701/2 |
| 2013/0205896 A1* | 8/2013 | Baechler | B62J 99/00 |
| | | | 73/493 |
| 2015/0015125 A1* | 1/2015 | Webber | B60B 1/041 |
| | | | 310/67 A |
| 2015/0099481 A1* | 4/2015 | Maitre | H04W 4/90 |
| | | | 455/404.2 |
| 2016/0253890 A1 | 9/2016 | Rabinowitz et al. | |
| 2016/0262661 A1 | 9/2016 | Sarkar et al. | |

FOREIGN PATENT DOCUMENTS

| | | |
|---|---|---|
| CN | 104337667 A | 2/2015 |
| CN | 104382307 A | 3/2015 |
| CN | 104382308 A | 3/2015 |
| CN | 104522954 A | 4/2015 |
| CN | 204351233 U | 5/2015 |
| DE | 10318929 B3 | 8/2004 |
| DE | 102012024039 A2 | 6/2014 |

* cited by examiner

MOBILITY AID MONITORING SYSTEM WITH MOTION SENSOR AND TRANSCEIVER

CROSS REFERENCE TO RELATED APPLICATION

This application claims priority to and the benefit of U.S. Ser. No. 62/509,167, titled "A Method for Monitoring Sleep Patterns, Nighttime Bathroom Usage, Wandering, and Potential Falls using a Passive Monitoring System for a Walking Aid User" and filed May 21, 2017, the disclosure of which is hereby incorporated by reference in its entirety.

BACKGROUND

Mobility aids are often used by patients that have health issues that limit their mobility. For example, the patient may be suffering from health issues associated with one or more of age, illness, or injury. Mobility aids may help these patients get around independently. Examples of mobility aids include canes, walkers, scooters, braces, wheelchairs, and crutches.

Falls, generally among the elderly, result in much healthcare spending. Mobility aids are meant to reduce falls by providing stability to a patient. However, mobility aids can go unused, often when little human supervision is present. Non-use of aids unnecessarily increases the risk of falling.

Fitness among those prone to falls is essential to reducing fall risk. Often, physicians and therapists will suggest a walking regimen for a patient in order to strengthen leg muscles. Feedback concerning the completion of such a regimen is often unavailable to the physicians or therapist.

Technology is enabling elderly people to live more independently through use of emergency response systems, in-home cameras, and other monitoring systems. Families, caregivers, healthcare professionals, and emergency personnel can monitor patients remotely, responding to various conditions relating to lifestyle, health, or safety.

SUMMARY

In general terms, this disclosure is directed to a system for monitoring a mobility aid. In one possible configuration and by non-limiting example, a monitoring system includes an attachable monitoring device that attaches to a mobility aid and a stationary communication node that communicates with the attachable monitoring device.

One aspect is an apparatus that includes a wheel attachment assembly, a motion sensor, and a transceiver. The wheel attachment assembly is configured to be removably attached to a wheel of a mobility aid. The motion sensor is configured to measure rotation of the wheel attachment assembly. The transceiver is in electronic communication with the motion sensor and configured to transmit data based on measurements from the motion sensor.

Another aspect is a system that includes a monitoring device and a stationary communication node. The monitoring device is configured to removably attach to a mobility aid and includes a transceiver and a motion sensor. The motion sensor is configured to measure motion of the monitoring device. The stationary communication node is configured to communicate with the monitoring device.

Yet another aspect is a method. The method includes receiving data generated by an attachable monitoring device for a mobility aid and determining that the data satisfies an alert condition. The method also includes generating an alert based on the alert condition being satisfied. In some implementations, the method also includes the steps of receiving data generated by a wearable device that includes a motion sensor and is configured to be worn by a patient, and determining that the data generated by the wearable device indicates that the patient is moving and the data generated by the attachable monitoring device indicates that the mobility aid is stationary.

The details of one or more aspects are set forth in the accompanying drawings and description below. Other features and advantages will be apparent from a reading of the following detailed description and a review of the associated drawings. It is to be understood that the following detailed description is explanatory only and is not restrictive of the claims.

DETAILED DESCRIPTION

Figure 1:
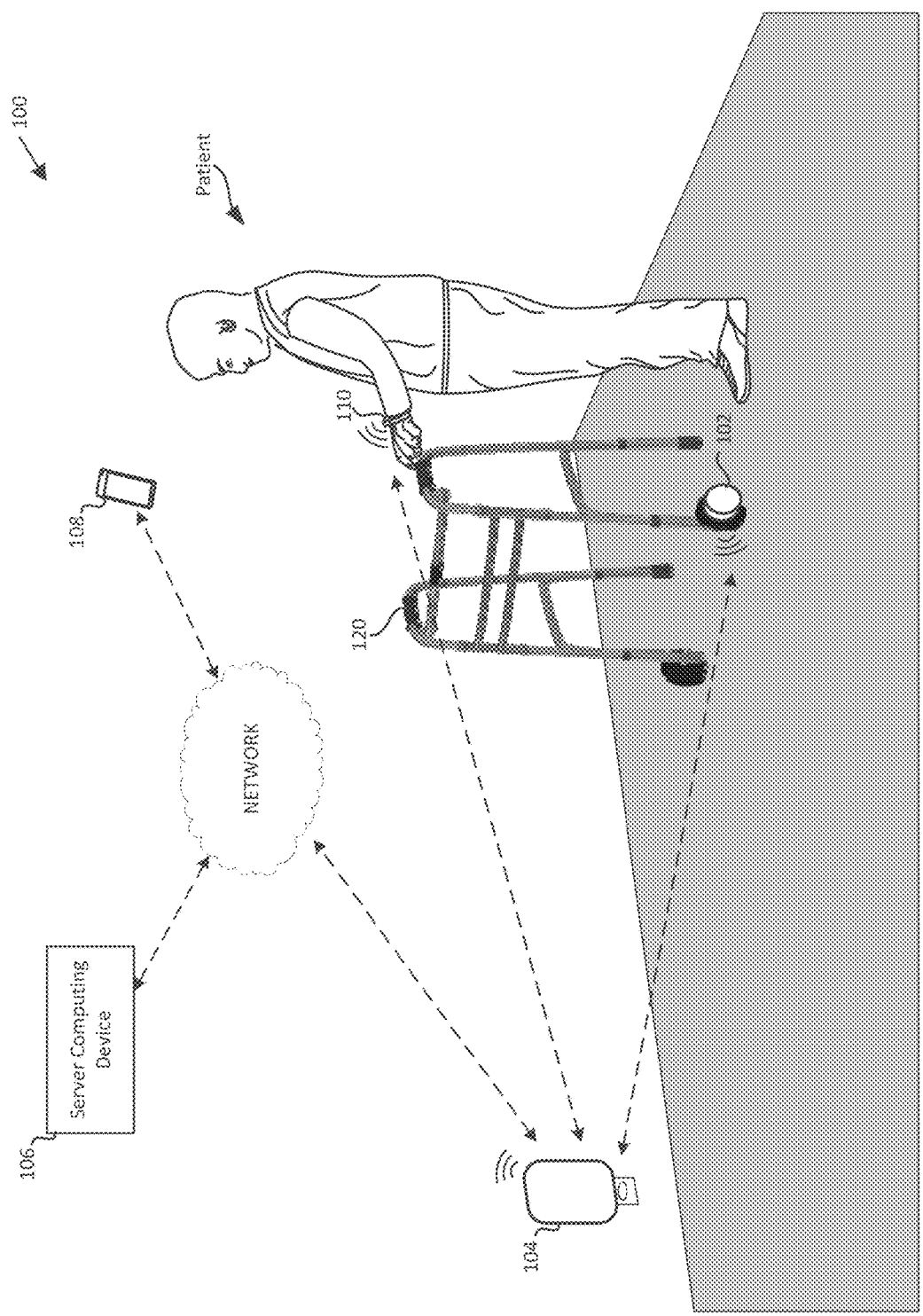
FIG. 1 is a schematic diagram of an implementation of a mobility aid monitoring system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates to a mobility aid monitoring system. The mobility aid monitoring system may include a monitoring device that attaches to a mobility aid so as to move with the mobility aid. The monitoring device may, for example, attach to a side surface of a wheel of a walker. The monitoring device may measure movement of the mobility aid. For example, the monitoring device may measure rotations of the wheel of a walker to determine when the walker is being used and how far a patient has traveled with the walker.

The monitoring system may also include a communication node that is configured to communicate with the monitoring device via a wireless communication protocol. Upon the occurrence of various events, the monitoring device may communicate with the communication node to transmit data related to use of a mobility aid. For example, the monitoring device may communicate with the communication node in response to detecting the beginning of mobility event based on movements of the mobility aid. A mobility event is a group of movements detected by the monitoring device and determined to belong to a single, substantially continuous activity by the monitoring device. For example, a mobility event may correspond to a walk across a room.

The monitoring device may also communicate with the communication node at various intervals or scheduled times regardless of whether any motion has been sensed. These periodic communications may serve to indicate one or more of the proximity of the monitoring device to the communication node, the continued functioning of the monitoring device (e.g., the monitoring device has not run out of batteries), and the absence of measured motion by the monitoring device.

In some implementations, the communication node may determine a signal strength associated with any communications received from the monitoring device. The signal strength, for example, may correlate to the distance between the monitoring device and the communication node.

The monitoring system may also include a server computing device that is configured to communicate with the communication node over a network, such as the Internet. The communication node may relay data received from the monitoring device and, in some implementations, associated signal strength measurements, to the server communication node. The server computing device may store the data and provide an interface for the patient and other users, such as caregivers and family members, to access the data.

In some implementations, the monitoring system may selectively generate alerts based upon the measurements captured by the monitoring device. For example, the monitoring system may generate alerts based on detecting a period of inactivity that exceeds an inactivity threshold. In some implementations, the inactivity threshold varies by time of day (e.g., the inactivity threshold may lower after an expected wake-up time). Some implementations also generate alerts based on the number of and types of mobility events detected during the night. Some nighttime mobility events may be classified as bathroom visits, for example, and an alert may be generated if the number of mobility events classified as bathroom visits exceeds a threshold. In some implementations, alerts are generated based on determining that the user is moving around without using the mobility aid (e.g., based on activity recorded by a wearable device).

There are many potential benefits of monitoring this type of information in patients or elderly individuals. Sleep patterns (bedtime and wakeup) can be correlated to an illness or depression. Excessive bathroom usage, increases in bathroom usage, or extended stays in the bathroom can be correlated to many illnesses, such as prostate cancer or a urinary tract infection. Wandering can be a symptom of a mental illness. And falls among elderly individuals continue to be costly and deadly for a number of reasons. Nighttime walking is generally to be avoided in elderly adults, since they tend to be more susceptible to balance-loss than during the day.

The systems and methods disclosed herein provide many advantages that are not available with conventional systems. Some conventional systems use a wearable device to monitor a patient or elderly individual. These wearable devices may miss activities that occur at night because the wearable device may be taken off or forgotten during the night time. In contrast, since the patient will typically still use the mobility aid at night, these movements will not be missed by implementations of the system described herein. Additionally, some conventional systems use stationary monitoring devices to detect motion within a physical space. These systems may not be able to distinguish between movements from multiple individuals. Additionally, a stationary monitory device may need to be placed in each room of a living space to track movement within each of those rooms. Further, this type of system cannot distinguish between movements made with a mobility aid and movements made without a mobility aid and thus cannot encourage use of a mobility aid. In contrast, implementations of the systems described herein can operate with only a single stationary communication node and can generate alerts when movement is detected without using a mobility aid.

FIG. 1 is a schematic diagram of an implementation of a mobility aid monitoring system 100. The mobility aid monitoring system 100 monitors the movement of the mobility aid. In some implementations, the mobility aid monitoring system 100 includes a monitoring device 102, a communication node 104, a server computing device 106, a client computing device 108, and a wearable device 110. Also shown in FIG. 1, is a mobility aid 120.

The monitoring device 102 is a device that attaches to a mobility aid 120 and measures motion of the mobility aid 120. In some implementations, the monitoring device 102 attaches to the mobility aid 120. When the patient uses the mobility aid 120 to move around, the monitoring device 102 will detect that movement. Based on this detected movement, the monitoring device 102 may determine when the patient is using the mobility aid 120 and for how long the patient uses the mobility aid 120. Although most of the examples described herein relate to implementations in which a monitoring device 102 is separate from and attached to a mobility aid 120, implementations in which the monitoring device 102 is integral with the mobility aid 120 are possible too.

The communication node 104 is a device that communicates with the monitoring device 102. For example, the communication node 104 may communicate with the monitoring device 102 via a wireless communication protocol such as the BlueTooth® Low Energy (LE) communication protocol. The communication node 104 may also communicate with the server computing device 106 over a network such as the Internet. For example, the communication node 104 may access the network to communicate with the server computing device 106 via a wireless or wired communication protocol.

In some implementations, the communication node 104 is a stationary device that is configured be statically placed in a particular location such as near the patient's bed. For example, the monitoring device 102 may transmit data about measured movements to the communication node 104 at various times, such as at scheduled times, after various intervals, or upon detecting a mobility event. When a communication is received from the monitoring device 102, the communication node 104 may determine a signal strength associated with the communication. The signal strength may be indicative of the distance between the communication node 104 and the monitoring device 102 and/or the location of the monitoring device 102. Although the example shown in FIG. 1 includes a single communication node, some implementations include multiple communication nodes that are statically positioned in multiple locations in which the patient may use the mobility aid 120.

The server computing device 106 is a computing device that communicates with the communication node 104. In some implementations, the server computing device 106 may receive data generated by the monitoring device 102 that is relayed by the communication node 104. In some implementations, the server computing device 106 associates the received data with the patient and stores the data. The server computing device 106 may include an interface that allows the patient and other users to access the data. For example, the server computing device 106 may maintain user accounts for the patient and one or more caregivers or family members of the patient. The server computing device 106 may also store configuration information for the patient. One example of the configuration data is a mobility aid parameter that is usable to determine distance from measurements captured by the monitoring device 102. Other examples of the configuration data include alert settings and time zone settings.

The client computing device 108 is a computing device that is used by a user to interact with the system 100. For example, the patient (or a caregiver or family member of the patient) may use the client computing device 108 to access measurement data generated by the monitoring device 102 to review the patient's activities. The number of activities and types of activities may be indicative of potential health issues or risks that should be addressed. The client computing device 108 can be any type of computing device, including but not limited to desktop computers, laptop computers, tablet computers, smartphones, and other types of computing device.

The wearable device 110 is a device worn by the patient. The wearable device 110 may detect movement of the patent. In some implementations, the mobility aid monitoring system 100 may determine that the patient is walking without using the mobility aid 120 based on the wearable device 110 detecting movement while the monitoring device 102 does not detect movement. In these instances, the mobility aid monitoring system 100 may generate an alert, for example, to remind the patient to use the mobility aid 120. Examples of the wearable device 110 include but are not limited to shoe pods, necklaces, clip-on devices, and wristbands.

Figure 2:
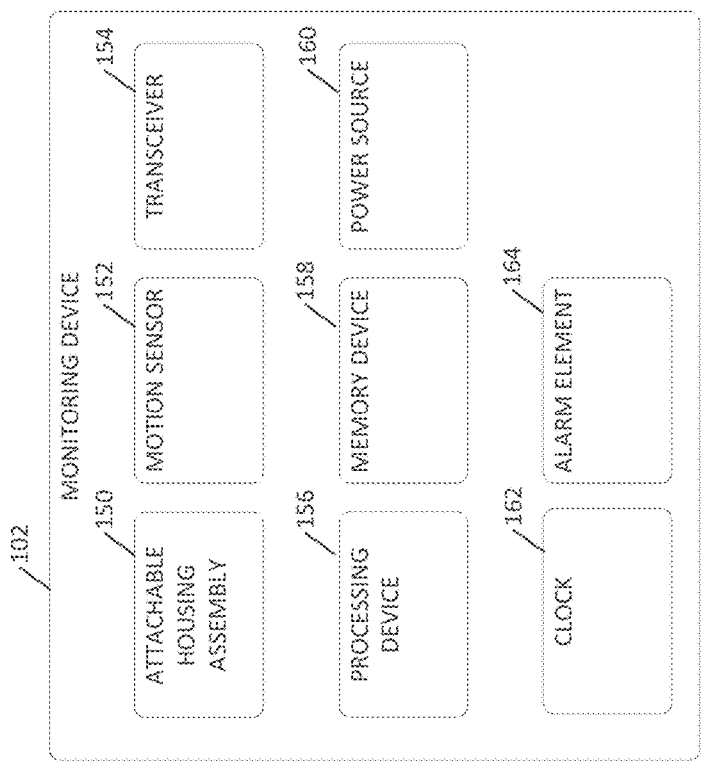
FIG. 2 is a schematic block diagram of an implementation of the monitoring device of FIG. 1.

FIG. 2 is a schematic block diagram of an implementation of the monitoring device 102. In this example, the monitoring device 102 includes an attachable housing assembly 150, a motion sensor 152, a transceiver 154, a processing device 156, a memory device 158, a power source 160, a clock 162, and an alarm element 164.

The attachable housing assembly 150 is a mechanical structure that is configured to hold at least some of the other components of the monitoring device 102 and to attach the monitoring device 102 to a mobility device. In some implementations, the attachable housing assembly 150 is formed from a non-conductive material, such as plastic, to reduce interference with radio frequency (RF) signals sent to/from the monitoring device 102. For example, the attachable housing assembly 150 may formed from one or more pieces of molded plastic. The attachable housing assembly 150 may include structural components that are configured to facilitate attachment of the monitoring device 102 to the mobility aid. Various types of structural components may be included based on the type of mobility aid to which the monitoring device 102 is configured to attach. For examples, the attachable housing assembly 150 may include various apertures through which fasteners (e.g., screws, tying mechanism, etc.) may pass to secure the monitoring device 102 to the mobility aid.

The motion sensor 152 is a device that is configured sense motion of the monitoring device 102, which can then be used to infer motion and orientation of the mobility aid. The inferred motion may be used to determine how far a patient moves using the mobility aid. The orientation may be used to detect whether the mobility aid has fallen over. For example, an alert may be generated upon detecting that the mobility aid has fallen over. In some implementations, the motion sensor 152 includes an inertial motion unit (IMU). The IMU can detect motion, movement, and/or acceleration of the monitoring device 102. The IMU may include various different types of sensors such as, for example, an accelerometer, a gyroscope, a magnetometer, and other such sensors. A position and/or orientation of the monitoring device 102 may be detected and tracked based on data provided by the sensors included in the IMU. Some implementations of the IMU include three orthogonally disposed accelerometers. In some implementations, the motion sensor 152 includes a Hall effect sensor, a reed switch, or an optical sensor.

The transceiver 154 is a device that transmits and receives communication signals. For example, the transceiver 154 may be configured to communicate with the communication node 104. For example, the transceiver 154 may receive and transmit RF signals in accordance with a low-energy wireless communication protocol, such as the BlueTooth LE protocol. Beneficially, when the transceiver 154 is configured to communicate using a low-energy wireless communication protocol the drain on the power source is reduced.

The processing device 156 includes one or more devices that are capable of executing instructions, such as instructions stored by the memory device 158, to perform various tasks associated with mobility-aid monitoring. For example, the processing device 156 may include one or more of microcontrollers, central processing units (CPUs), digital signal processors (DSPs), and/or a graphics processing units (GPUs).

The memory device 158 can include one or more non-transitory computer-readable storage media. The memory device 158 may store instructions and data that are usable by the monitoring device 102 to perform at least some of the functions described herein.

The power source 160 provides power for the monitoring device 102. In some implementations, the power source 160 includes one or more batteries.

The clock 162 stores and tracks time. In some implementations, the clock 162 includes a real-time clock chip. The time values generated by the clock 162 are used by the processing device 156 to timestamp measurements captured by the motion sensor 152. In some implementations, the time values are also used to determine when to initiate at least some of the communications with the communication node 104 (e.g., communications on intervals or schedules).

The alarm element 164 is a component that generates an alarm to attempt to get a patient's attention (or another person's attention). In some implementations, the alarm element 164 includes one or more lights, speakers, or haptic feedback devices. For example, the alarm element 164 may include a light emitting diode (LED) that may be activated by the processing device 156 to indicate the occurrence of an alarm condition. The alarm element 164 may also emit a sound upon the occurrence of alarm condition. As another example, the alarm element 164 may vibrate or provide another form of haptic feedback to indicate the occurrence of an alarm condition.

Figure 3:
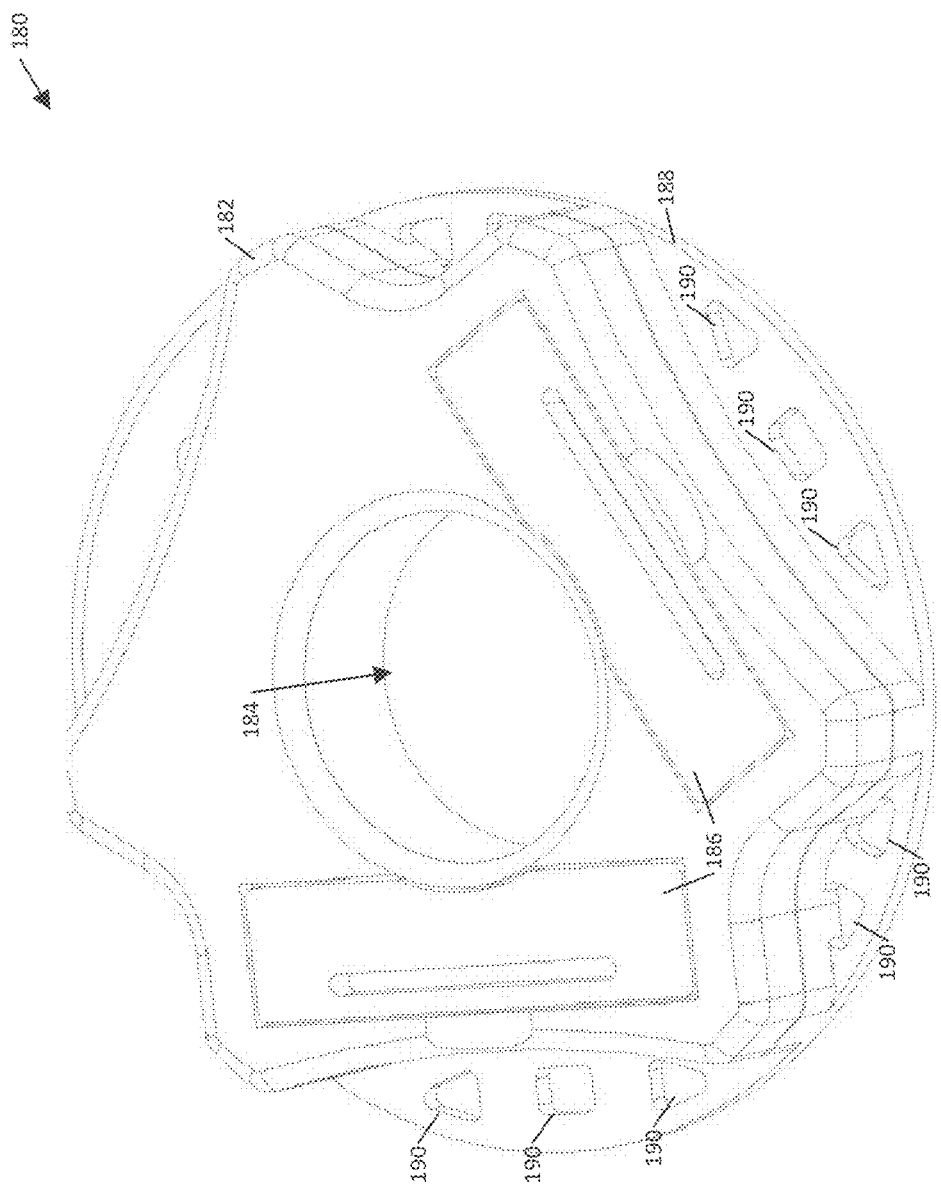
FIG. 3 is a schematic diagram of an implementation of an attachable housing assembly of FIG. 2 configured to attach to a wheel of a mobility aid such as a walker.

FIG. 3 is a schematic diagram of an implementation of an attachable housing assembly 180 configured to attach to a wheel of a mobility aid such as a walker. The attachable housing assembly 180 is an example of the attachable housing assembly 150. In this example, the attachable housing assembly 180 includes a shell 182, a hub aperture 184, a battery compartment assembly 186, and a wheel attachment assembly 188. In some implementations, the wheel attachment assembly 188 includes multiple apertures 190.

In some implementations, the shell 182 defines an interior chamber in which at least some of the components of the monitoring device 102 are disposed. The shell 182 may be formed from a rigid non-conductive material such as plastic. Although not shown in this example, the shell 182 may include one or more apertures through which components of or signals emitted by the alarm element 164 may pass (e.g., light or sound) out from the interior chamber. Additionally, the shell 182 may define the hub aperture 184 that is configured to fit over a hub of a wheel of the mobility aid 120. In some implementations, the hub aperture 184 allows the monitoring device 102 to abut a side surface of the wheel (e.g., a sidewall of the wheel).

The battery compartment assembly 186 is formed within the shell 182 and includes one or more chambers configured to receive batteries. The battery compartment assembly 186 may include a panel that can be removed or repositioned to permit access to the chambers to install or replace batteries.

The wheel attachment assembly 188 is a component of the attachable housing assembly 180 that is configured to attach to the mobility aid 120. In this example, the wheel attachment assembly 188 includes a flat disc-shaped structure that is configured to attach to a side surface of a wheel of mobility aid so that the monitoring device 102 rotates as the wheel rotates. In this manner, the motion sensor 152 of the monitoring device 102 will sense motion that is substantially similar to the motion of the wheel.

In this example, the wheel attachment assembly 188 includes multiple apertures 190 that are configured to receive fasteners, such as screws or cable ties, to secure the monitoring device 102 to the wheel. Other implementations may include other structures for attaching the monitoring device 102 to the mobility aid 120. For example, the wheel attachment assembly 188 may include a clasp to attach to a leg of the mobility aid 120.

Figure 4:
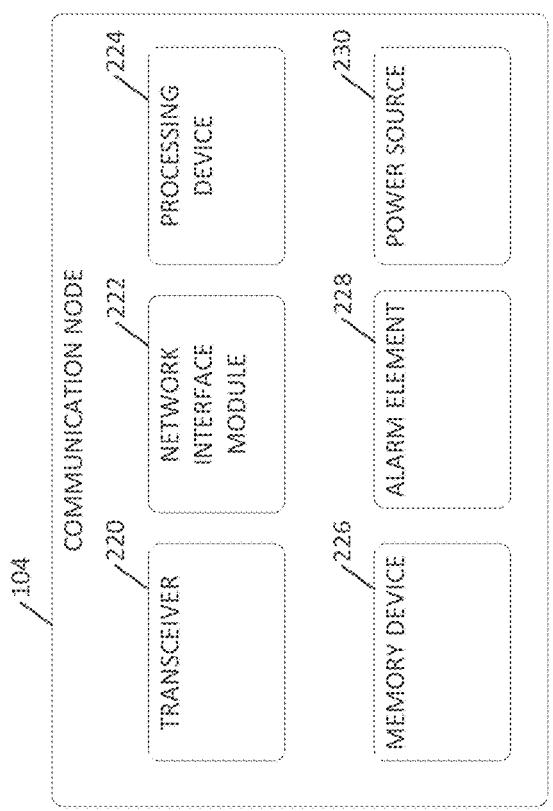
FIG. 4 is a schematic block diagram of an implementation of the communication node of FIG. 1.

FIG. 4 is a schematic block diagram of an implementation of the communication node 104. In this example, the communication node 104 includes a transceiver 220, a network interface module 222, a processing device 224, a memory device 226, an alarm element 228, and a power source 230.

The transceiver 220 is a device that transmits and receives communication signals. For example, the transceiver 220 may be configured to communicate with the monitoring device 102. For example, the transceiver 220 may be similar to the transceiver 154 of the monitoring device 102.

The network interface module 222 includes one or more devices for communicating with other computing devices, such as the server computing device 106. The network interface module 222 may communicate via wireless or wired networks, such as the Internet. For example, the network interface module 222 may include one or more of a Wi-FI communication module, a cellular network communication module, an Ethernet communication module, or other network communication modules.

The processing device 224 includes one or more devices that are capable of executing instructions, such as instructions stored by the memory device 158, to perform various tasks associated with mobility-aid monitoring, including for example receiving data from the monitoring device 102 and transmitting data to the server computing device 106. The processing device 224 may include components similar to those discussed with respect to the processing device 156.

The memory device 226 can include one or more non-transitory computer-readable storage media. The memory device 226 may store instructions and data that are usable by the communication node 104 to perform at least some of the functions described herein.

The alarm element 228 is a component that generates an alarm to attempt to get a patient's attention (or another person's attention). The alarm element 228 may be similar to the previously described alarm element 164.

The power source 230 provides power for the communication node 104. In some implementations, the power source 230 receives power from a wall outlet. The power source 230 may include a converter circuit to convert power from the form provide by the wall outlet to the form required by the components of the communication node 104 (e.g., by converting from AC to DC, transforming voltage or current). Additionally, the power source 230 may one or more batteries that can be used instead of the power received from the wall outlet or as a backup to the wall outlet.

Figure 5:
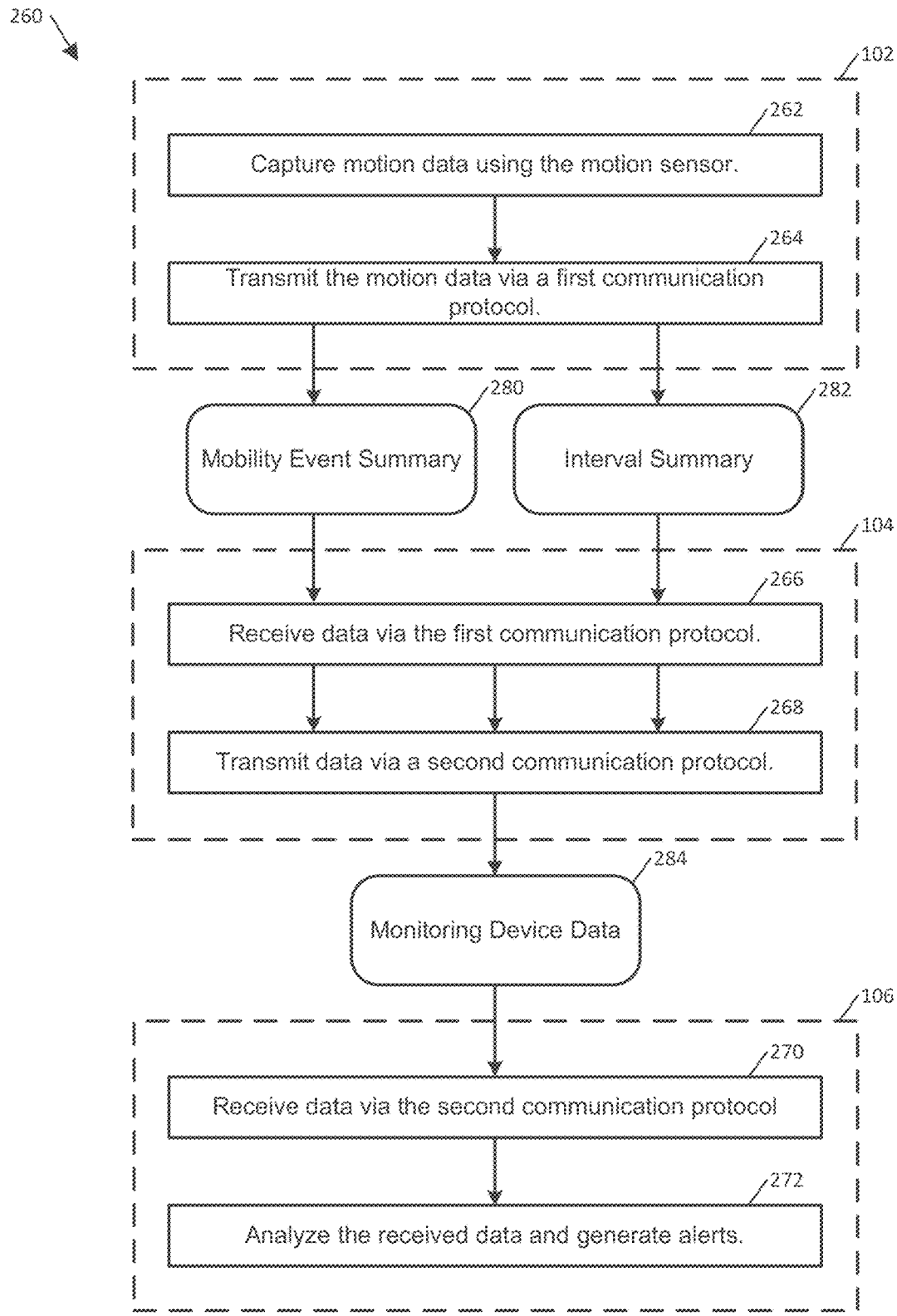
FIG. 5 is a diagram of an example method of monitoring a mobility aid, in accordance with implementations described herein.

FIG. 5 is a diagram of an example method 260 of monitoring a mobility aid, in accordance with implementations described herein. This diagram also shows an example data flow between the monitoring device 102, the communication node 104, and the server computing device 106 performing as the method 260 is performed. This data flow is an example, and in some implementations, the data transmitted between the monitoring device 102, the communication node 104, and the server computing device 106 varies. The operations described below may also be performed by different components of the system 100 in some implementations.

At operation 262, motion data is captured using the motion sensor. For example, operation 262 may be performed by the monitoring device 102. In some implementations, capturing the motion data includes capturing a series of measurements that correspond to a motion property of the monitoring device 102 (e.g., the orientation of the monitoring device 102, the acceleration of the monitoring device 102 in one more directions) over a time period. The motion measurements may be associated with a timestamp. The captured motion data may also include timestamps associated with at least some of the measurements. Based on the series of measurements, a cumulative motion value may be determined for the time period (e.g., a number of rotations of the monitoring device 102, a number of steps). In some situations, the series of measurements may indicate that the monitoring device 102 has been stationary during the corresponding time period. Additionally, the orientation of the mobility device may be inferred based on measurements from the monitoring device 102. For example, some implementations include a three-axis accelerometer arrangement that can determine the orientation of the mobility aid 120. Rotational changes in orientation of the monitoring device 102 relative to the axis of a wheel of the mobility aid 120 may be interpreted as aided movements by the patient. Tipping changes in orientation of the monitoring device 102 may instead be interpreted as falls. In some implementations, an alert may be generated based on identifying a tipping change in orientation of the monitoring device 102 that is not corrected within a defined time period.

At operation 264, the motion data is transmitted via a first communication protocol. For example, the motion data may be transmitted by the monitoring device 102 to the communication node 104 using the BlueTooth LE communication protocol. In some implementations, the captured motion data is summarized by the monitoring device to generate a mobility event summary 280 that is then transmitted.

For example, the monitoring device 102 may identify a start and end of a mobility event based on the sequence of captured motion data. The start of a mobility event may be identified based on detecting motion when a mobility is not currently in progress (e.g., the monitoring device 102 may be in a non-mobility event state). Upon detecting the start of a mobility event, the monitoring device 102 may transition to a mobility event state. Additionally, in some implementations, the monitoring device 102 transmits data indicating that a mobility event has started. For example, the monitoring device 102 may broadcast a connection request (e.g., advertise its presence per the BlueTooth LE protocol) for a time period to the communication node 104 or another system. After the time period, the monitoring device 102 may stop broadcasting so as to conserve power. If another device, such as the communication node 104, responds to the connection request, the monitoring device 102 may then establish a connection with that other device and transmit data to that other device indicating that a mobility event has started.

During the mobility event, the monitoring device 102 may store the sequence of measurements captured by the motion sensor 152 on the memory device 158. In some implementations, the monitoring device 102 also transmits the measurements captured by the motion sensor 152 to another device such as the monitoring device 102 or the client computing device 108. As described further below, the server computing device 106 may generate a user interface that displays various types of information during the course of an ongoing mobility event.

The mobility event may then continue until a time period that exceeds an end-of-event threshold elapses during which additional motion is not detected. In some implementations, the end-of-event threshold is at least five second, at least ten seconds, or at least fifteen seconds. In some implementations, the end-of-event threshold is a time value selected from the range of five to thirty seconds.

When the end of a mobility event is detected, the monitoring device 102 may generate the mobility event summary 280 based on the measurements stored in the memory device 158 during the mobility event. The mobility event summary 280 may include, for example, one or more of a start timestamp, an end timestamp, a duration time value, a cumulative motion value, and a distance value. The cumulative motion value may be calculated based on combining the motion measurements during the sequence of movements. Non-limiting examples of the cumulative motion value include a number of rotations and a number of steps. The distance value may be determined based on applying a mobility aid parameter (e.g., wheel diameter) or a patient specific parameter (e.g., stride length) to the cumulative motion value. A daily (or other duration of time) mobility summary value may also be updated at the end of a mobility event. The mobility event summary 280 may also include other properties of the mobility event such as a gait analysis score that identifies shuffling or other potential issues. The gait analysis may be based on a distributions in the distance traveled/speed during the course of a mobility event.

The mobility event summary 280 may be stored in the memory device 158. Additionally, the monitoring device 102 may broadcast a connection request to the communication node 104 and, after establishing a connection, transmit the mobility event summary to the communication node 104. In some implementations, after transmitting the mobility event summary 280, the monitoring device 102 transmits the stored data (not shown) that corresponds to the measurements captured by the motion sensor 152. In this manner, the mobility event summary can be used or presented more quickly than the full data set (e.g., the mobility event summary 280, which may transfer more quickly because it is smaller, can be presented while the full data set for a mobility event is being transferred). In some implementations, a time period summary (not shown) for an entire time period (e.g., a daily summary) is transmitted at a scheduled time, such as at midnight each day. In at least some of these implementations, some or all of the mobility event summaries are transmitted after the time period summary (i.e., rather than at the completion of the mobility event).

The monitoring device 102 may also generate and transmit interval summaries, such as the interval summary 282, periodically. For example, the monitoring device 102 may transmit an interval summary each time an interval time period elapses (e.g., an interval summary may be transmitted every five minutes, every ten minutes, every fifteen minutes). For example, the interval summary 282 may include a timestamp. In some implementations, the interval summary 282 may include additional information such as a cumulative motion value, which would be zero when no motion is detected during the interval. The interval summary 282 may serve as a check-in that the communication node 104 or the server computing device 106 can use to distinguish between times when the mobility aid 120 is nearby but not being used and times when the monitoring device 102 cannot communicate with the communication node 104 (e.g., when the monitoring device 102 and the mobility aid 120 are in a different location).

At operation 266, data is received via the first communication protocol. For example, the communication node 104 may receive the mobility event summary 280 or the interval summary 282 from the monitoring device 102. In some implementations, the communication node 104 determines a signal strength value for any data received from the monitoring device 102. In some implementations, the signal strength value corresponds to the strength of the signal received from the monitoring device 102 via the first communication protocol. For example, the signal strength value may be a relative received signal strength (RSSI) of the received radio signal. The communication node 104 may then store the received data and signal strength value in the memory device 226.

At operation 268, data is transmitted via second communication protocol. For example, the communication node 104 may transmit monitoring device data 284 to the server computing device 106 via the Internet using a WiFi or cellular network communication protocol. In some implementations, the communication node 104 relays the data it receives from the monitoring device 102 to the server computing device 106. In some implementations, the communication node 104 also transmits a signal strength value along with the relayed data. The communication node 104 may also include an identifier of the monitoring device 102 that generated the monitoring device data 284.

At operation 270, data is received via the second communication protocol. For example, the server computing device 106 may receive the monitoring device data 284 from the communication node 104. The server computing device 106 may then associate the received data with a patient based on an identifier of the monitoring device 102 that generated the monitoring device data 284. The received monitoring device data 284 may then be stored by the server computing device 106.

At operation 272, the received data is analyzed and alerts are generated. For example, the server computing device 106 may apply a mobility aid parameter associated with the patient to a cumulative motion value associated with a mobility event to calculate the distance the patient traveled during the mobility event. In some implementations, the server computing device 106 analyzes the data to identify events that may indicate potential health concerns, such as wandering during the night, frequent bathroom visits during the night, periods of inactivity, changes in gait, late wake-ups, or failures to use the mobility aid 120. For example, the received data may be evaluated against one or more alert conditions to determine when to generate an alert. The alert conditions may be specific to a patient. Additionally, alert conditions may be specific to a patient and an associated caregiver or family member. For example, a caregiver or family member may define specific alert conditions for which an alert should be generated.

Generating an alert may comprise producing an audio, visual, or haptic alarm on the monitoring device 102 or communication node 104. For example, the server computing device 106 may transmit data to the communication node 104 that indicates the monitoring device 102 or communication node 104 should generate an alarm. Similar alerts may also be triggered on the wearable device 110. In some implementations, e-mail, SMS, or phone call alerts are also generated.

In some implementations, an alert is initially directed to a patient based on an alert condition being satisfied. For example, if an inactivity streak exceeds an inactivity threshold an alert may be directed to the patient to check whether the patient needs help. In response to the alert, the patient may take an action to clear the alert. If, however, the patient does not clear the alert within a response time period, a second alert may be generated. The second alert may be directed to a secondary user associated with the patient. The second alert may indicate to the secondary user that the patient may be in need of help. In some instances, this process can continue to generate additional alerts that are directed to additional users until the alert is cleared.

Various other properties of the received data may be determined during the analysis. For example, some mobility events may be used to identify bedtime or wakeup for the patient. Bedtime may be identified based on a mobility event that ends near the communication node 104 (which is typically near the patient's bed) and is not followed by any additional mobility events for a period of time. If there are multiple mobility events that match these conditions, the multiple mobility events are compared against average daily bedtime, duration of time before the next mobility event, and distance of walking before the current event. Two possible bedtime events can be compared using an equation such as below:

$$\text{bedtime score} = a*(\text{duration\_1} - \text{duration\_2}) + b*(\text{distance\_1} - \text{distance\_2}) + c*((\text{time\_2} - \text{averageBedtime})/(\text{time\_1} - \text{averageBedtime}),$$

Where duration is the time before the next mobility event, distance is the total distance traversed during a set period of time before the event, time is the timestamp of the event, averageBedtime is the typical bedtime of the user, and a, b, and c are tuning coefficients for the calculation. If score is positive, then mobility event 1 is a more likely bedtime than mobility event 2.

Wakeup times can be identified by analyzing the mobility events too. For example, if a mobility event moves away from the communication node 104, it is identified as a potential wakeup event. To remove false positives and walking events in which the user goes back to bed, the signal strength, total distance traversed after the potential wakeup and daily average wakeup after event are compared. For example, the total distance of all mobility events 30 minutes after a potential wakeup event can be used to determine if a user returned to bed or if they are up for the day. Two possible wakeup events can be compared using an equation such as below:

$$\text{score} = a(\text{duration\_1} - \text{duration\_2}) + b(\text{distance\_1} - \text{distance\_2}) + c|(\text{time\_2} - \text{averageWakeup})/(\text{time\_1} - \text{averageWakeup}),$$

Where duration is the time since the last mobility event, distance is the total distance traversed during a set period of time after the event, time is the timestamp of the event, averageWakeup is the typical wakeup of the user, and a, b, and c are tuning coefficients for the calculation. If score is positive, then mobility event 1 is a more likely wakeup than mobility event 2. In some implementations, alerts are generated when deviations from the typical wakeup or bedtime events are identified.

Although in FIG. 5, the step of analyzing the monitoring device data 284 and generating alerts is shown as being performed by the server computing device 106, other implementations are possible too. For example, either the monitoring device 102 or the communication node 104 may analyze data captured by the monitoring device 102 and generate alerts if appropriate.

Figure 6:
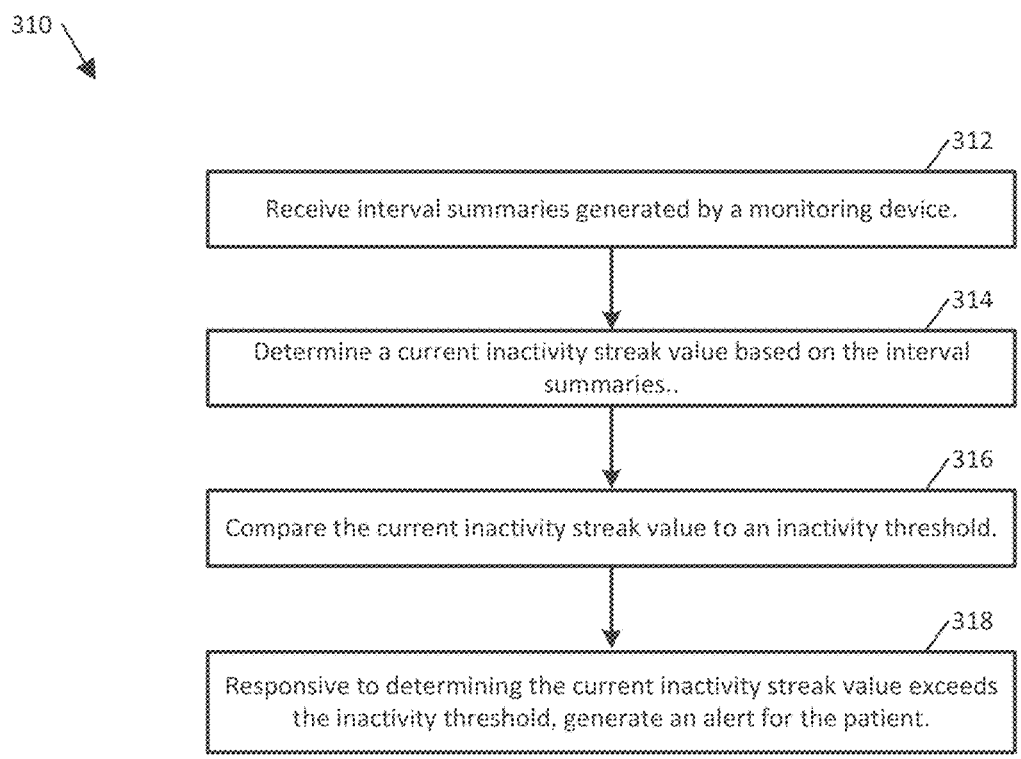
FIG. 6 is a diagram of an example method of generating an alert based on inactivity, in accordance with implementations described herein.

FIG. 6 is a diagram of an example method 310 of generating an alert based on inactivity, in accordance with implementations described herein. In some implementations, the method 310 is performed by the server computing device 106. The method 310 may also be performed by the monitoring device 102 or the communication node 104.

At operation 312, interval summaries generated by the monitoring device 102 are received. As described above, the interval summaries include data indicating whether any motion was detected during a particular interval.

At operation 314, a current inactivity streak value is determined based on the interval summaries. For example, the inactivity streak value may be a time value that represents the number of intervals in which no motion (or less than an activity threshold amount of motion) is detected by the monitoring device 102. In this manner, the current inactivity streak value will continue to grow until an interval summary indicates that motion has been detected by the monitoring device 102.

At operation 316, the current inactivity streak value is compared to an inactivity threshold. In some implementations, the inactivity streak threshold value is a patient-specific value that can be set on the server computing device 106. Additionally, some implementations include multiple inactivity thresholds (e.g., a first threshold for day time, a second threshold for night time). If the current inactivity streak value exceeds the inactivity threshold, the alert condition associated with inactivity is considered satisfied and the method proceeds to operation 318.

At operation 318, an alert is generated for the patient. Techniques for generating alerts have been discussed above. Additionally, in some implementations, the inactivity alert threshold is specific to a user associated with a patient and the alert may be directed to that user.

Figure 7:
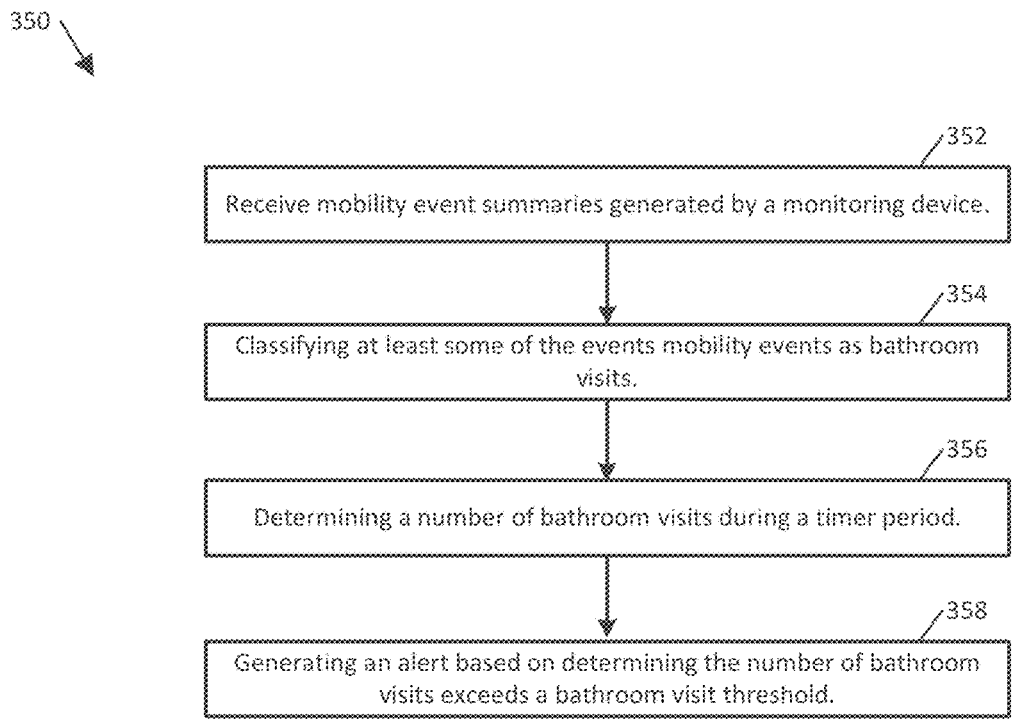
FIG. 7 is a diagram of an example method of generating an alert based on bathroom visits, in accordance with implementations described herein

FIG. 7 is a diagram of an example method 350 of generating an alert based on bathroom visits, in accordance with implementations described herein. In some implementations, the method 350 is performed by the server computing device 106. The method 350 may also be performed by the monitoring device 102 or the communication node 104.

At operation 352, mobility event summaries generated by the monitoring device 102 are received. As described above, the mobility event summaries include data about mobility events detected by the monitoring device 102. For example, the mobility event summaries may include at least a time value and a duration value. In some implementations, the mobility event summaries also include a signal strength value.

At operation 354, at least some of the mobility events are classified as bathroom visits. For example, the mobility events may be classified as bathroom visits based on the time value and the duration value. In some situations, the classification is also based on a preceding mobility event. For example, if two mobility events of short durations occur during the night and are separated by a short time period (e.g., a walk to and from the bathroom), one of the mobility events may be classified as a bathroom visit. In some implementations, the signal strength value is also used to classify the mobility events as bathroom visits. As noted above, the signal strength value may be indicative of the distance between the monitoring device 102 and the communication node 104. Accordingly, the signal strength at the end of a mobility event may be compared to an expected signal strength for a bathroom visit based on the distance between the bathroom and the communication node 104. Based on the comparison and/or the other factors described above, the mobility event may be classified as a bathroom visit.

Figure 8:
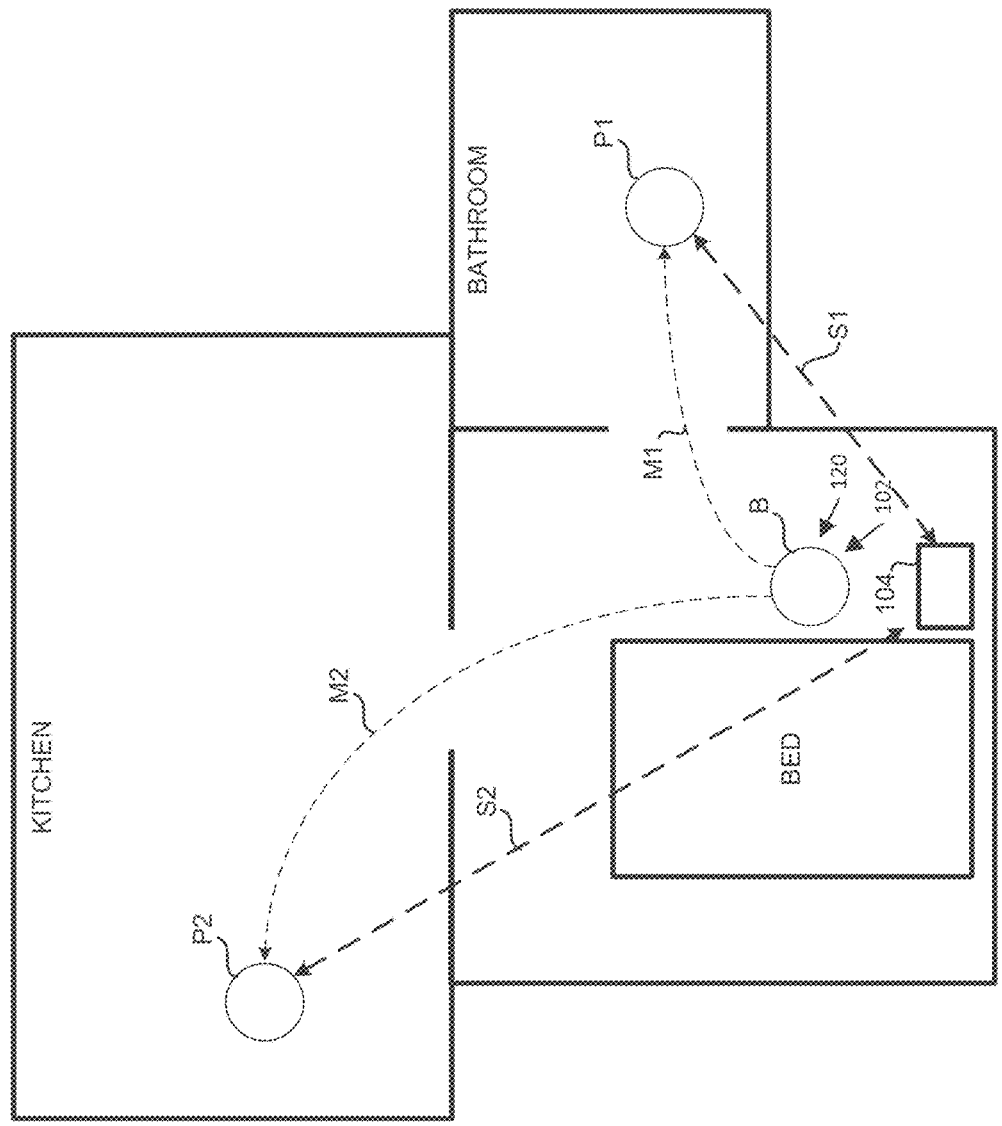
FIG. 8 is a schematic block diagram of mobility events detected by the system of FIG. 1 within an example living space.

Turning now to FIG. 8, an example overhead view of a living space is shown. The living space includes a bedroom, bathroom, and kitchen. Overlaid on the view of the living space are a mobility event and M1 and a mobility event M2. In the first mobility event M1, the patient moved the mobility aid 120 with the attached monitoring device 102 from a base position B near the patient's bed to a position P1 in the bathroom. While the mobility aid 120 was disposed at P1 (i.e., in the bathroom), the monitoring device 102 transmitted the communication signal S1 to the communication node 104, which is located near the patient's bed. In the second mobility event M2, the patient moved the mobility aid 120 with the attached monitoring device 102 from the base position B to a position P2 in the kitchen. While the mobility aid 120 was disposed at P2 (i.e., in the kitchen), the monitoring device 102 transmitted the communication signal S2 to the communication node 104, which is located near the patient's bed. In at least some implementations, the communication node 104 determines the signal strength of the signals S1 and S2. These determined signal strengths may then be used in classifying mobility events.

Returning now to FIG. 7, at operation 356, a number of bathroom visits during a time period is determined. In some implementations, the time period is a night. At operation 358, an alert is generated based on determining that the number of bathroom visits exceeds a bathroom visit threshold. For example, the alert may be directed to a caregiver who can consider whether to check the patient for urinary tract infections, prostate issues, or other conditions.

Although the method 350 relates to bathroom visits, other implementations classify mobility events differently. For example, some implementations selectively classify mobility events as night wanderings based on one or more of the time, duration, and signal strength of the mobility event. If the number of night wanderings exceeds a night wandering threshold, a night wandering alert may be generated.

Figure 9:
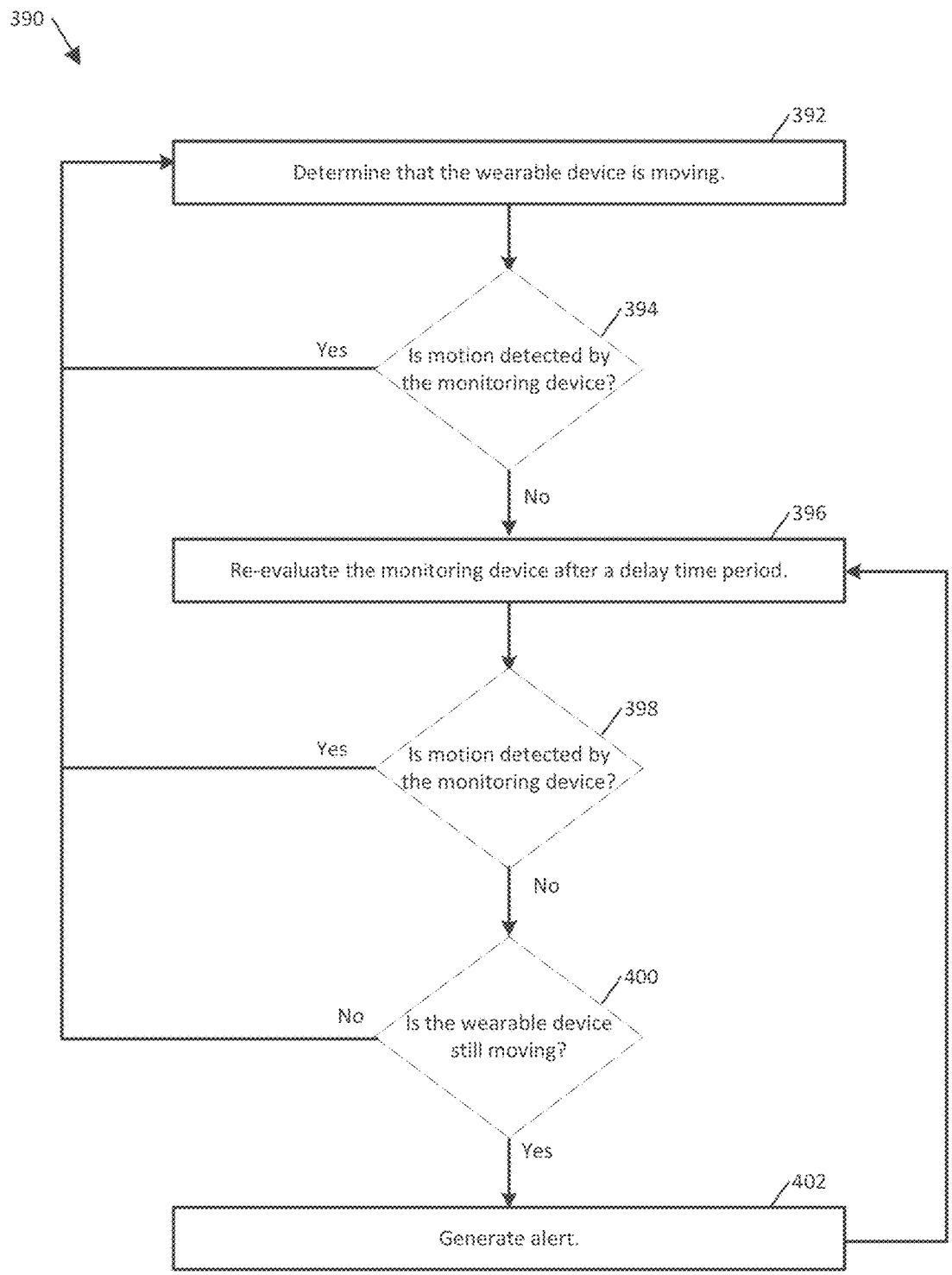
FIG. 9 is a diagram of an example method of generating an alert based on determining a patient is moving without using the mobility aid, in accordance with implementations described herein.

FIG. 9 is a diagram of an example method 390 of generating an alert based on determining a patient is moving without using the mobility aid, in accordance with implementations described herein. For example, the method 390 may be performed by the monitoring device 102 or the wearable device 110, which may communicate directly with each other. In some implementations, the communication node 104 communicates with the monitoring device 102 and the wearable device 110 and performs at least some operations of the method 390.

At operation 392, it is determined that the wearable device 110 is moving. For example, it may be determined that the wearable device 110 is moving based on the wearable device 110 detecting motion. After it is determined that the wearable device is moving, the method proceeds to operation 394.

At operation 394, it is determined whether motion is detected by the monitoring device 102. If motion is detected, the method returns to operation 392. If motion is not detected, the method continues to operation 396.

At operation 396, the monitoring device 102 is re-evaluated for motion after a delay time period. Various implementations use various delay time periods. The re-evaluation may help prevent false alarms.

At operation 398, it is again determined whether motion is detected by the monitoring device 102 after the delay time period. If motion is detected, the method returns to operation 392. If motion is not detected, the method continues to operation 400.

At operation 400, it is determined whether the wearable device 110 is still moving. By confirming that the wearable device 110 is still moving, some false alarms may be prevented. If the wearable device 110 is still moving, the method continues to operation 402. If the wearable device 110 is not still moving, the method returns to operation 392.

At operation 402 an alert is generated. The alert may be audio, visual, or haptic and may be generated by the monitoring device 102 or the wearable device 110. The alert may encourage the patient to use the mobility aid 120 when moving. After generating the alert, the method may return to operation 396 to re-evaluate the monitoring device 102.

Figure 10:
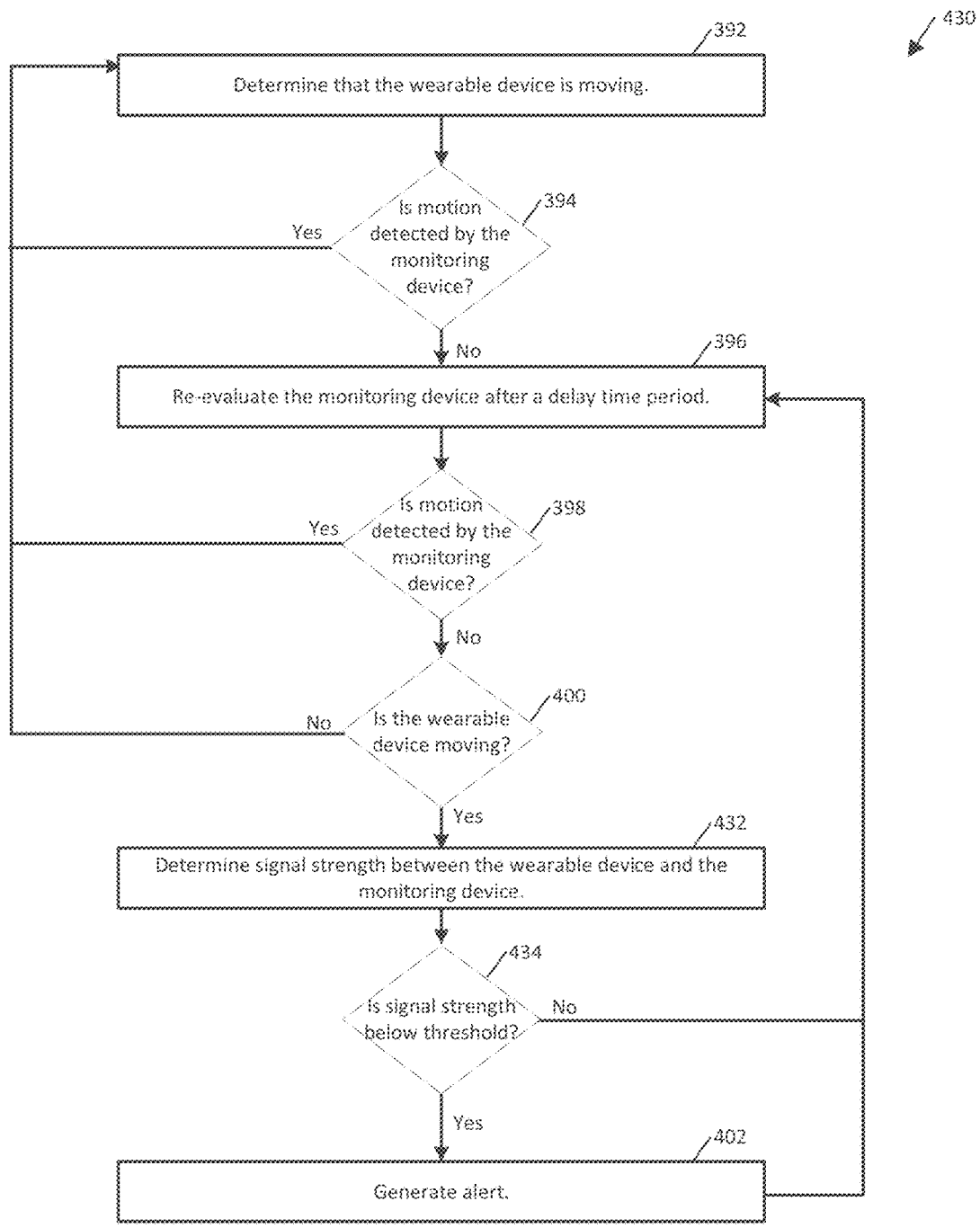
FIG. 10 is a diagram of an example method of generating an alert based on determining a patient is moving without using the mobility aid, in accordance with implementations described herein.

FIG. 10 is a diagram of an example method 430 of generating an alert based on determining a patient is moving without using the mobility aid, in accordance with implementations described herein. The method 430 is similar to the method 390 except that the method 430 also takes into account the signal strength for communication between the monitoring device 102 and the wearable device 110. For example, the method 430 may generate an alarm when a patient is moving without using the mobility aid 120 and has moved away from the mobility aid 120. The method 430 may be performed by the monitoring device 102 or the wearable device 110, which may communicate directly with each other. In some implementations, the communication node 104 communicates with the monitoring device 102 and the wearable device 110 and performs at least some operations of the method 430.

The method 430 includes the operation 392, 394, 396, 398, and 400, which have been previously described with respect to the method 390. However, in the method 430 if it is determined that the wearable device is moving at operation 400, the method continues to operation 432. At operation 432, a signal strength between the wearable device 110 and the monitoring device 102 is determined.

At operation 434, it is determined whether the signal strength is a below a threshold value. If the signal strength is below the threshold value, the method proceeds to operation 402, where an alert is generated. If the signal strength is not below the threshold, the method returns to operation 396.

Figure 11:
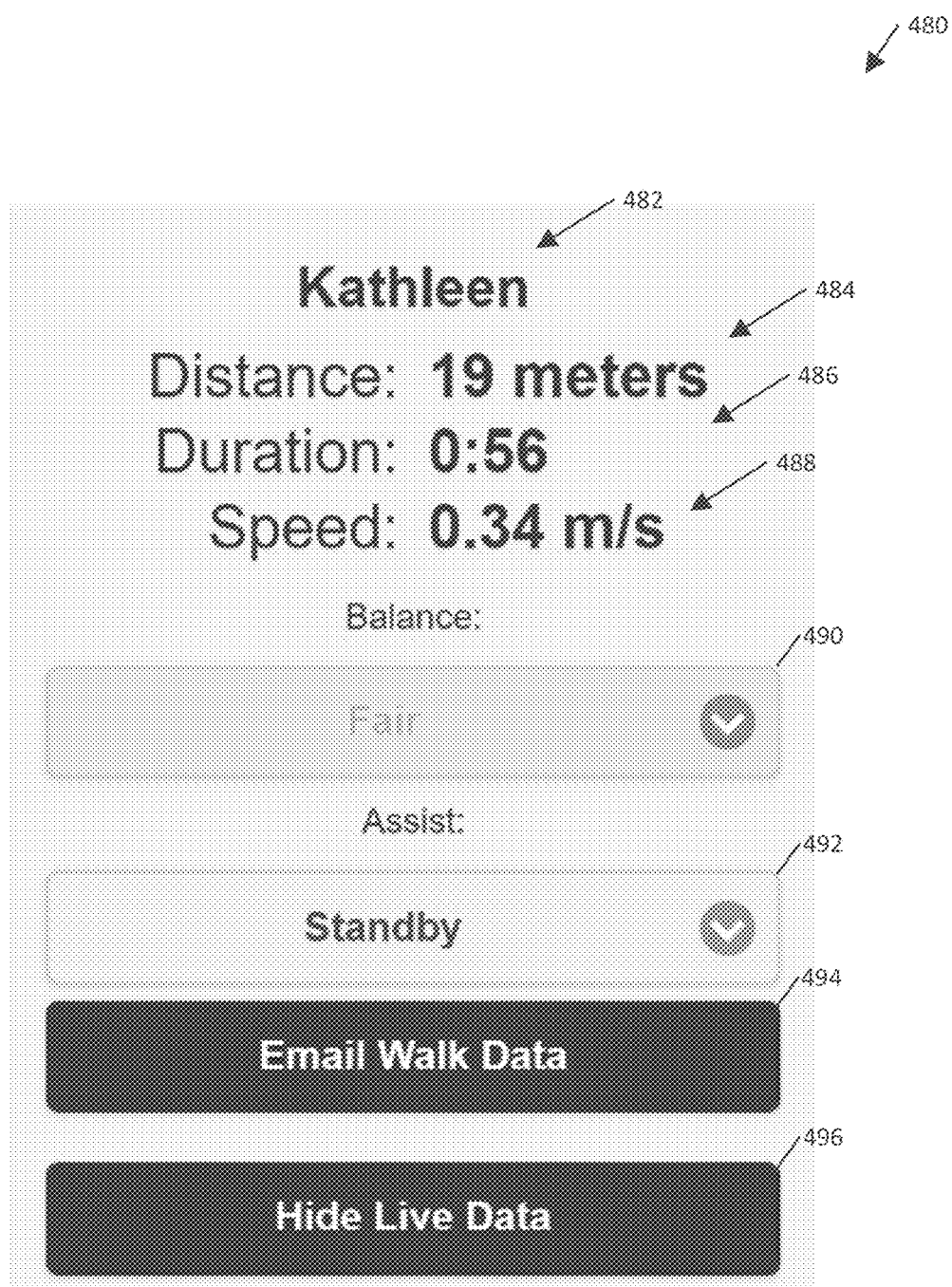
FIG. 11 is a schematic diagram of an example user interface screen in accordance with implementations described herein.

FIG. 11 is a schematic diagram of an example user interface screen 480 in accordance with implementations described herein. For example, the client computing device 108 may display the example user interface screen 480 to allow a user to view and/or interact with data from the monitoring device 102. In some implementations, the example user interface screen 480 is displayed during the course of a mobility event to provide real-time information to a caregiver or real-time feedback to a patient.

In this example, the example user interface screen 480 a patient indicator 482, a distance parameter 484, a duration parameter 486, a speed parameter 488, a balance element 490, an assist element 492, an e-mail element 494, and a live data toggle element 496.

The patient indicator 482 may be a visual display that indicates the patient from which the displayed data was collected (or is being collected). The patient indicator 482 may include one or more of the patient's name, an identifier associated with the patient, an image of the patient.

The distance parameter 484, the duration parameter 486, and the speed parameter 488 are examples of mobility event data that may be display during or after a mobility event.

The balance element 490 is a field in which a caregiver can record a balance status for the patient. In some implementations, the balance element 490 is a drop down list of descriptive values related to the patient's balance that a caregiver may select. Similarly, the assist element 492 is a field in which a caregiver can record an assist status for the patient, which may be selected from a dropdown list. Once selected, the values of the balance element 490 and the assist element 492 may be stored in association with the patient. Other implementations may include addition, different, or fewer fields for recording information about the patient.

The e-mail element 494 is a user-acuatable control that triggers transmission of an e-mail containing data about the displayed mobility event.

The data toggle element 496 is a user-actuatable control that is usable to disable or enable the collection and display of live data.

Figure 12:
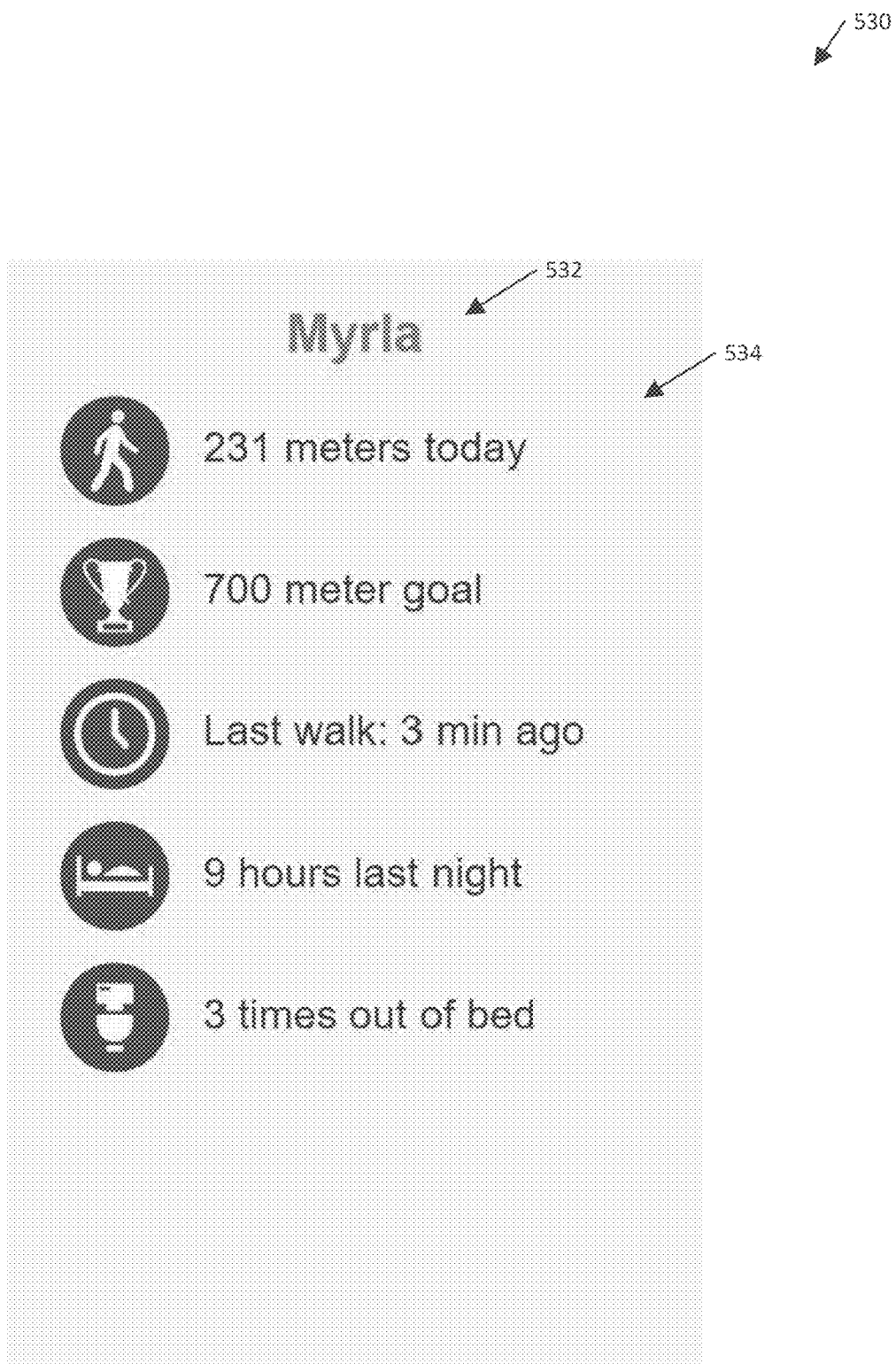
FIG. 12 is a schematic diagram of an example user interface screen in accordance with implementations described herein.

FIG. 12 is a schematic diagram of an example user interface screen 530 in accordance with implementations described herein. For example, the client computing device 108 may display the example user interface screen 530 to allow a user to view and/or interact with summary data from the monitoring device 102. In some implementations, the example user interface screen 530 includes a patient indicator 532 and a summary panel 534. The patient indicator 532 may be similar to the patient indicator 482. The summary panel 534 displays various information about the patient, including information captured by the monitoring device 102 or information/settings entered by a user. In this example, the summary panel includes a distance traveled during the current day, a goal distance for the day, information about the most recently recorded mobility event, the amount of time the patient slept (or was in bed) the previous night, and the number of times the patient left bed the previous night.

Figure 13:
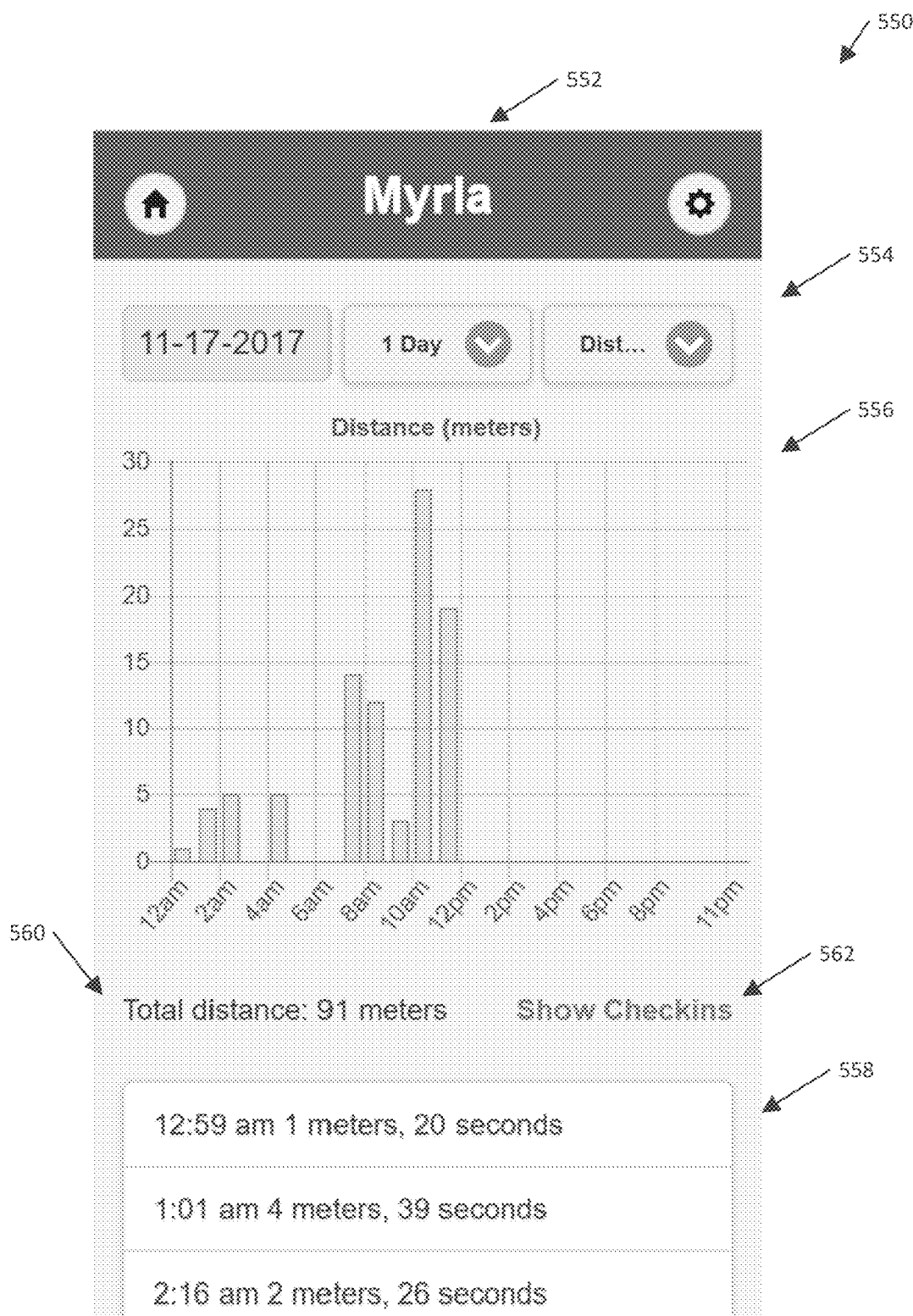
FIG. 13 is a schematic diagram of an example user interface screen in accordance with implementations described herein.

FIG. 13 is a schematic diagram of an example user interface screen 550 in accordance with implementations described herein. For example, the client computing device 108 may display the example user interface screen 550 to allow a user to view and/or interact with data from the monitoring device 102. In some implementations, the example user interface screen 550 includes a patient indicator 552, a selection panel 554, a graph panel 556, an event table 558, and an information field 560. The patient indicator 552 may be similar to the patient indicator 482. The selection panel 554 includes various user-actuatable controls that may be used to adjust which data are displayed and how the data are displayed on the user interface screen 550. The graph panel 556 includes a graph of data captured by the monitoring device 102. In this example, the graph panel 556 shows a graph of distance traveled by the patient during each hour of a day (as selected using the selection panel 554). The event table 558 shows a list of mobility events during the selected time period. The information field 560 can show information about the data captured during the selected time period. In this example, the information field 560 shows the total distance traveled during the selected time period. The user interface screen 550 also includes a check-in view control 562 that can be actuated to view check-ins (i.e., interval summaries) transmitted by the monitoring device 102 during the selected time period.

Figure 14:
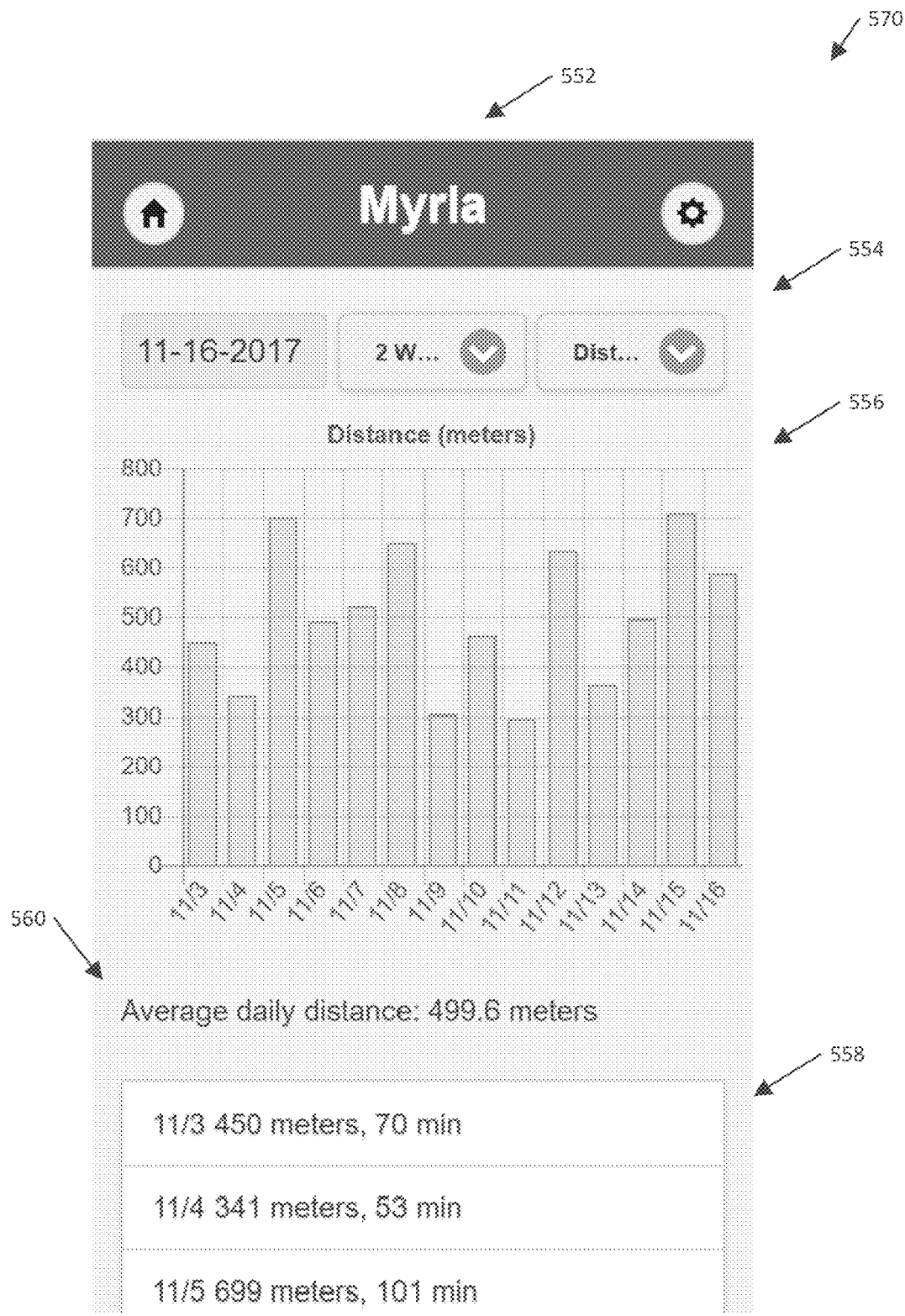
FIG. 14 is a schematic diagram of an example user interface screen in accordance with implementations described herein.

FIG. 14 is a schematic diagram of another user interface screen 570 in accordance with implementations described herein. For example, the client computing device 108 may display the example user interface screen 570 to allow a user to view and/or interact with data from the monitoring device 102. The user interface screen 570 is similar to the user interface screen 550, except that the selection panel 554 is set to show two weeks of data. Accordingly, the graph panel 556 shows a graph of distance traveled by day during the selected two-week time period and the event table 558 shows mobility events during that time period. In this example, the information field 560 shows the average distance traveled per day during the selected time period. Although not shown, the user interface screen 570 can also include the check-in view control 562 or other user-actuatable controls.

Figure 15:
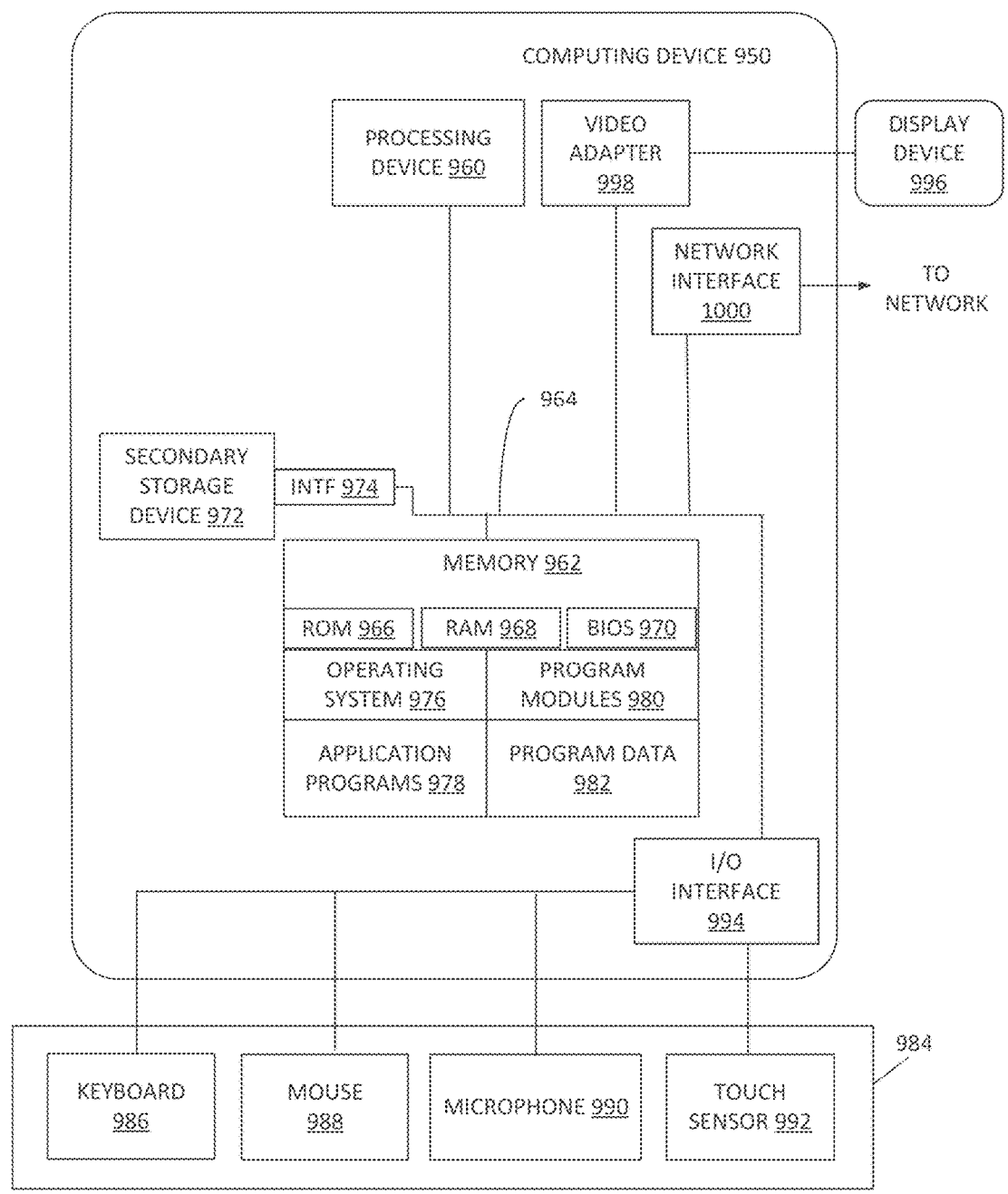
FIG. 15 illustrates an example architecture of a computing device, which can be used to implement aspects according to the present disclosure.

FIG. 15 illustrates an example architecture of a computing device 950 that can be used to implement aspects of the present disclosure, including any of the plurality of computing devices described herein, such as the server computing device 106, the client computing device 108, or any other computing devices that may be utilized in the various possible embodiments.

The computing device illustrated in FIG. 15 can be used to execute the operating system, application programs, and software modules described herein.

The computing device 950 includes, in some embodiments, at least one processing device 960, such as a central processing unit (CPU). A variety of processing devices are available from a variety of manufacturers, for example, Intel or Advanced Micro Devices. In this example, the computing device 950 also includes a system memory 962, and a system bus 964 that couples various system components including the system memory 962 to the processing device 960. The system bus 964 is one of any number of types of bus structures including a memory bus, or memory controller; a peripheral bus; and a local bus using any of a variety of bus architectures.

Examples of computing devices suitable for the computing device 950 include a desktop computer, a laptop computer, a tablet computer, a mobile computing device (such as a smart phone, an iPod® or iPad® mobile digital device, or other mobile devices), or other devices configured to process digital instructions.

The system memory 962 includes read only memory 966 and random access memory 968. A basic input/output system 970 containing the basic routines that act to transfer information within computing device 950, such as during start up, is typically stored in the read only memory 966.

The computing device 950 also includes a secondary storage device 972 in some embodiments, such as a hard disk drive, for storing digital data. The secondary storage device 972 is connected to the system bus 964 by a secondary storage interface 974. The secondary storage devices 972 and their associated computer readable media provide nonvolatile storage of computer readable instructions (including application programs and program modules), data structures, and other data for the computing device 950.

Although the example environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory computer-readable media. Additionally, such computer readable storage media can include local storage or cloud-based storage.

A number of program modules can be stored in secondary storage device 972 or system memory 962, including an operating system 976, one or more application programs 978, other program modules 980 (such as the software engines described herein), and program data 982. The computing device 950 can utilize any suitable operating system, such as Microsoft Windows™, Google Chrome™ OS or Android, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 950 through one or more input devices 984. Examples of input devices 984 include a keyboard 986, mouse 988, microphone 990, and touch sensor 992 (such as a touchpad or touch sensitive display). Other embodiments include other input devices 984. The input devices are often connected to the processing device 960 through an input/output interface 994 that is coupled to the system bus 964. These input devices 984 can be connected by any number of input/output interfaces, such as a parallel port, serial port, game port, or a universal serial bus. Wireless communication between input devices and the interface 994 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 996, such as a monitor, liquid crystal display device, projector, or touch sensitive display device, is also connected to the system bus 964 via an interface, such as a video adapter 998. In addition to the display device 996, the computing device 950 can include various other peripheral devices (not shown), such as speakers or a printer.

When used in a local area networking environment or a wide area networking environment (such as the Internet), the computing device 950 is typically connected to the network through a network interface 1000, such as an Ethernet interface or WiFi interface. Other possible embodiments use other communication devices. For example, some embodiments of the computing device 950 include a modem for communicating across the network.

The computing device 950 typically includes at least some form of computer readable media. Computer readable media includes any available media that can be accessed by the computing device 950. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 950.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 15 is also an example of programmable electronics, which may include one or more such computing devices, and when multiple computing devices are included, such computing devices can be coupled together with a suitable data communication network so as to collectively perform the various functions, methods, or operations disclosed herein.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. An apparatus comprising:
 a wheel attachment assembly, the wheel attachment assembly configured to be removably attached to a wheel of a mobility aid;
 a motion sensor that includes an accelerometer assembly and is configured to measure rotation of the wheel attachment assembly based on measurements from the accelerometer assembly;
 a transceiver in electronic communication with the motion sensor and configured to transmit data based on measurements from the motion sensor;
 a processing device; and
 a memory device that stores instructions that when executed by the processing device, cause the apparatus to:
  identify a start of a mobility event based on measurements from the motion sensor;
  identify an end of the mobility event based on measurements from the motion sensor; and
  responsive to identifying the end of the mobility event, store summary data associated with the mobility event and broadcast a connection request.

2. The apparatus of claim 1, wherein the instructions further cause the apparatus to determine a distance of the mobility event based on a mobility aid parameter stored in the memory device.

3. The apparatus of claim 1, wherein the wheel attachment assembly is configured to removably attach to a side surface of the wheel.

4. The apparatus of claim 3, wherein the apparatus further comprises an aperture configured to receive a hub of the wheel.

5. A system comprising:
 a stationary communication node; and
 a monitoring device that is configured to removably attach to a mobility aid, the monitoring device including:
  a transceiver;
  a motion sensor configured to measure motion of the monitoring device;
  a processing device; and
  a memory device that stores instructions that when executed by the processing device, cause the monitoring device to:
   determine that an interval time period has elapsed;
   generate an interval summary indicating whether any motion was detected during the interval time period;
   broadcast a connection request directed to the communication node;
   establish a connection with the communication node;
   transmit the interval summary to the communication node;
   identify a start of a mobility event based on measurements from the motion sensor;
   identify an end of the mobility event based on measurements from the motion sensor; and
   responsive to identifying the end of the mobility event:
    store summary data associated with the mobility event;
    broadcast a connection request directed to the stationary communication node; and
    establish a connection with the stationary communication node.

6. The system of claim 5, wherein the monitoring device is configured to attach to a wheel of a walker so that the monitoring device rotates with the wheel.

7. The system of claim 5, wherein the stationary communication node includes a transceiver, a processing device, and a memory device that stores instructions that when executed by the processing device, cause the stationary communication node to:
 receive connection requests broadcast by the monitoring device;
 responsive to receiving a connecting request:
  establish a connection with the monitoring device;
  receive an interval summary;
  store the interval summary;
  determine a signal strength for the connection; and
  associate the signal strength with the stored interval summary.

8. The system of claim 7, wherein the instructions stored on the memory device of the stationary communication node further cause the stationary communication node to:
 determine an identifier of the monitoring device; and
 associate the identifier with the stored interval summary.

9. The system of claim 8, wherein the instructions stored on the memory device of the stationary communication node further cause the stationary communication node to transmit data received from the monitoring device to a server computing device, wherein the transmitted data includes the interval summary and the identifier.

10. The system of claim 9, further comprising the server computing device, the server computing device being configured to:
 associate the received data with a patient based on the identifier; and
 generate a user alert based on determining that an inactivity time threshold has been exceeded based on a plurality of interval summaries received from the communication node indicating that the monitoring device has detected less movement than a movement threshold.

11. The system of claim 5, wherein the instructions further cause the monitoring device to:
 identify a start of a mobility event based on measurements from the motion sensor;
 identify an end of the mobility event based on measurements from the motion sensor; and
 responsive to identifying the end of the mobility event:
  store summary data associated with the mobility event;
  broadcast a connection request directed to the stationary communication node;
  establish a connection with the stationary communication node; and
  transmit the summary data associated with the mobility event to the stationary communication node.

12. The system of claim 11, wherein the summary data associated with the mobility event includes a start time of the mobility event, a duration of the mobility event, and a cumulative motion value for the mobility event.

13. The system of claim 5, further comprising a wearable device that includes a transceiver and a motion sensor, wherein the wearable device is configured to:
 detect movement of a user based on the motion sensor;
 responsive to detecting movement, transmit data associated with the movement to the communication node; and
 wherein the communication node is configured to generate an alert upon receiving an indication from the wearable device that the user is moving and determining that the monitoring device is stationary.

14. A method comprising:
receiving data generated by an attachable monitoring device for a mobility aid, the data including mobility events that include time values and duration values of mobility events detected by a motion sensor of the monitoring device;
determining that the data satisfies an alert condition by:
classifying at least some of the mobility events as being bathroom visits based on the time values and duration values;
determining a number of bathroom visits during a time period; and
determining that the number of bathroom visits during the time period exceeds a bathroom visit threshold; and
generating an alert based on the alert condition being satisfied.

15. The method of claim 14, wherein generating an alert comprises:
generating an alert directed to a patient associated with the attachable monitoring device; and
responsive to determining that the patient has not responded to the alert within a response time period, generating a second alert directed to a secondary user associated with the patient.

16. The method of claim 14, wherein:
receiving data generated by the attachable monitoring device comprises receiving interval summaries that include cumulative distance information detected by a motion sensor of the monitoring device during a corresponding interval of time; and
determining that the data satisfies the alert condition comprises:
determining a current inactivity streak value based on the received data;
comparing the current inactivity streak value to an inactivity threshold; and
determining the current inactivity streak value exceeds the inactivity threshold.

17. The method of claim 14, wherein the mobility events include a signal strength value that corresponds to a determined signal strength between the attachable monitoring device and a stationary communication node and the classifying is based on signal strength values.

18. The method of claim 14, wherein:
receiving data generated by the attachable monitoring device comprises receiving mobility event data that indicates a mobility event has started; and
generating an alert comprises:
generating a mobility event alert;
transmitting the mobility event to a mobile computing device;
establishing a connection with the mobile computing device; and
streaming data generated by the attachable monitoring device to the mobile computing device.

19. The method of claim 14, further comprising:
determining a signal strength between the attachable monitoring device and a stationary communication node; and
determining that the signal strength and data satisfy an alert condition.

20. A system comprising:
a stationary communication node; and
a monitoring device that is configured to removably attach to a mobility aid, the monitoring device including:
a transceiver;
a motion sensor configured to measure motion of the monitoring device;
a processing device; and
a memory device that stores instructions that when executed by the processing device, cause the monitoring device to:
determine that an interval time period has elapsed;
generate an interval summary indicating whether any motion was detected during the interval time period;
broadcast a connection request directed to the communication node;
establish a connection with the communication node; and
transmit the interval summary to the communication node;
wherein the stationary communication node is configured to communicate with the monitoring device and includes:
a processing device; and
a memory device that stores instructions that when executed by the processing device, cause the stationary communication node to:
receive connection requests broadcast by the monitoring device;
responsive to receiving a connection request:
establish a connection with the monitoring device;
receive an interval summary;
store the interval summary;
determine a signal strength for the connection; and
associate the signal strength with the stored interval summary.

21. A system comprising:
a stationary communication node;
a monitoring device that is configured to removably attach to a mobility aid, the monitoring device including:
a transceiver; and
a motion sensor configured to measure motion of the monitoring device; and
a wearable device that includes a transceiver and a motion sensor, wherein the wearable device is configured to:
detect movement of a user based on the motion sensor;
responsive to detecting movement, transmit data associated with the movement to the stationary communication node; and
wherein the stationary communication node is configured to generate an alert upon receiving an indication from the wearable device that the user is moving and determining that the monitoring device is stationary.

22. A method comprising:
receiving data generated by an attachable monitoring device for a mobility aid;
determining that the data satisfies an alert condition by:
receiving data generated by a wearable device that includes a motion sensor and is configured to be worn by a patient; and
determining that the data generated by the wearable device indicates that the patient is moving and the data generated by the attachable monitoring device indicates that the mobility aid is stationary; and
generating an alert based on the alert condition being satisfied.

* * * * *